(12) United States Patent
Terunuma et al.

(10) Patent No.: US 11,328,434 B2
(45) Date of Patent: May 10, 2022

(54) OBJECT TRACKING DEVICE

(71) Applicant: UNIVERSITY OF TSUKUBA, Ibaraki (JP)

(72) Inventors: Toshiyuki Terunuma, Ibaraki (JP); Takeji Sakae, Ibaraki (JP)

(73) Assignee: UNIVERSITY OF TSUKUBA, Ibaraki (JP)

( * ) Notice: Subject to any disclaimer, the term of this patent is extended or adjusted under 35 U.S.C. 154(b) by 429 days.

(21) Appl. No.: 16/490,595

(22) PCT Filed: Mar. 1, 2018

(86) PCT No.: PCT/JP2018/007873
§ 371 (c)(1),
(2) Date: Sep. 2, 2019

(87) PCT Pub. No.: WO2018/159775
PCT Pub. Date: Sep. 7, 2018

(65) Prior Publication Data
US 2020/0005472 A1 Jan. 2, 2020

(30) Foreign Application Priority Data
Mar. 3, 2017 (JP) .............................. JP2017-041111

(51) Int. Cl.
*G06K 9/00* (2006.01)
*G06T 7/32* (2017.01)
(Continued)

(52) U.S. Cl.
CPC .............. *G06T 7/32* (2017.01); *A61N 5/1049* (2013.01); *G06K 9/6234* (2013.01); *G06T 7/246* (2017.01);
(Continued)

(58) Field of Classification Search
CPC .. G06T 7/32; G06T 7/55; G06T 7/246; A61N 5/1049; A61N 2005/1061; G06K 9/6234
See application file for complete search history.

(56) References Cited

U.S. PATENT DOCUMENTS 8,837,863 B2 * 9/2014 Homma .................. G06T 7/277
382/294
2005/0100208 A1 * 5/2005 Suzuki ................. G06T 7/0012
382/157

(Continued)

FOREIGN PATENT DOCUMENTS

JP  3053389 B1  6/2000
JP  4505639 B2  7/2010
(Continued)

OTHER PUBLICATIONS

International Search Report in PCT Application No. PCT/JP2018/007873, dated Jun. 5, 2018, 2pp.

*Primary Examiner* — Avinash Yentrapati
(74) *Attorney, Agent, or Firm* — Hauptman Ham, LLP

(57) ABSTRACT

An object tracking device includes a superimposed image creation unit configured to create a plurality of superimposed images in which each of a plurality of non-tracking object images which do not include a tracking object image feature is superimposed on a tracking object section image which includes a tracking object image feature; a discriminator creation unit configured to learn at least one of an image feature and position information of the tracking object, based on the plurality of superimposed images to create a discriminator; and a tracking object specifying unit configured to specify at least one of the image feature and the position information of the tracking object in a tracked image including the respective image features of the tracking object and an obstacle, based on the discriminator and the tracked image.

8 Claims, 10 Drawing Sheets

(51) Int. Cl.
*G06T 7/55* (2017.01)
*G06T 7/246* (2017.01)
*A61N 5/10* (2006.01)
*G06K 9/62* (2022.01)

(52) U.S. Cl.
CPC ........ *G06T 7/55* (2017.01); *A61N 2005/1061* (2013.01)

(56) References Cited

U.S. PATENT DOCUMENTS

| | | | |
|---|---|---|---|
| 2007/0297566 A1* | 12/2007 | Urano | A61N 5/1049 378/65 |
| 2010/0215234 A1* | 8/2010 | Yamada | G06T 7/55 382/131 |
| 2013/0129255 A1* | 5/2013 | Homma | G06T 11/60 382/294 |
| 2016/0175614 A1* | 6/2016 | Taguchi | G06K 9/6211 382/131 |
| 2017/0043184 A1* | 2/2017 | Mori | A61N 5/1037 |
| 2017/0312544 A1 | 11/2017 | Mori et al. | |
| 2019/0392589 A1* | 12/2019 | Hirakawa | G06T 7/246 |

FOREIGN PATENT DOCUMENTS

| | | | |
|---|---|---|---|
| JP | 2010-194053 A | 9/2010 |
| JP | 5610441 B2 | 10/2014 |
| JP | 2016-137007 A | 8/2016 |
| WO | 2015/125600 A1 | 8/2015 |

\* cited by examiner

FIG. 8

|  | Experimental Example 1 | Comparative Example 1 | Comparative Example 2 |
|---|---|---|---|
| Error [pixel] | Ave 0.22 (SD 1.7) | Ave 4.4 (SD 10.) | Ave 3.9 (SD 9.1) |
| Correlation | 0.997 | 0.113 | 0.256 |
| Jaccard Coefficient | Ave 0.918 (Max0.995, Min0.764) | — | — |

## OBJECT TRACKING DEVICE

RELATED APPLICATIONS

The present application is a National Phase of International Application No. PCT/JP2018/007873, filed Mar. 1, 2018, and claims priority based on Japanese Patent Application No. 2017-041111, filed Mar. 3, 2017.

TECHNICAL FIELD

The present invention relates to an object tracking device.

BACKGROUND ART

When performing radiation therapy, or the like, since a position of a target object (tumor, etc.) of treatment moves due to breathing or pulsation of a subject (patient), in order not to irradiate a site (normal site) other than the target object with radiation, it is required to capture an X-ray fluoroscopic image in real time, track the target object and specify its position, and irradiate with radiation, only when the target object has moved to an irradiation position. Further, in a technique of capturing an image, specifying and tracking the position of the target object, and guiding the radiation to the irradiation position, a so-called object tracking technique by guiding the image, generally uses the X-ray fluoroscopic image, but it is not limited thereto. For example, in addition to the X-ray fluoroscopic images, ultrasound images, magnetic resonance imaging (MRI) images, computed tomography (CT) images, and positron emission tomography (PET) images may also be used.

The following techniques are known as a technique for specifying and tracking the position of the target object.

Patent Document 1 (Japanese Patent No. 5610441) describes a technique of compensating for a deterioration in tracking performance assumed at the time of markerless tracking by X-ray fluoroscopy with extracorporeal information. That is, the above patent describes an object tracking technique, in which based on a template image including a therapeutic target object such as a cancer lesion, pattern matching is executed on each frame of an X-ray fluoroscopic image for detecting a position of the therapeutic target object during the treatment, and irradiation of therapeutic radiation is performed, when the position of the therapeutic target falls within a predetermined error range from a planned irradiation position, and in order to minimize an irradiation deviation due to pseudo-periodic movement caused by breathing etc., within a time (phase) window (set based on the movement of a body surface) suitable as an irradiation timing. Furthermore, Patent Document 1 also describes that, in order to increase a determination accuracy of a therapeutic target position, pattern matching is performed using a non-tracking object such as a thoracic diaphragm or a bone, etc. different from the therapeutic target as information on a reference position.

Patent Document 2 (Japanese Patent No. 3053389) describes a technique for inserting a metal marker into a patient's body to increase the tracking accuracy of tracking near a tumor with the X-ray fluoroscopy. That is, the above patent describes a technique of specifying a position of a tumor marker in three dimensions by capturing a tumor marker embedded near the tumor to be the target object of treatment by transmitting X-ray from a plurality of directions, and performing template matching with the template image of the previously registered tracking object (tumor) marker by using a density normalized cross-correlation method.

Patent Document 3 (Japanese Patent No. 4505639) describes a technique of specifying a position of a tumor marker by performing template matching by using the density normalized cross-correlation method similar to Patent Document 2, and acquiring time-series positional data in advance, such that the position of the tumor marker at the current time is estimated from the previously acquired data.

Patent Document 4 (International Publication No. WO 2015/125600) describes a technique of specifying a position of a therapeutic target site in each breathing phase by executing template matching created for different breathing phases on continuously acquired X-ray images. According to the technique described in Patent Document 4, the template is created by calculating a deformation amount of X-ray images in a treatment object site between different breathing phases from three-dimensional X-ray image data including the position of the treatment object site in the reference breathing phase and the treatment object sites in a plurality of continuous breathing phases, and acquiring positions of the treatment object site in each breathing phase.

PRIOR ART DOCUMENT

Patent Document

[Patent Document 1] Japanese Patent No. 5610441 (paragraphs "0010," "0013" to "0016," and FIGS. 1A and 1B and FIG. 2)

[Patent Document 2] Japanese Patent No. 3053389 (paragraphs "0035" to "0046," and FIGS. 1A and 1B and FIG. 2)

[Patent Document 3] Japanese Patent No. 4505639 (paragraphs "0024" to "0029") [Patent Document 4] International Publication NO. 2015/125600 (paragraph "0010")

SUMMARY OF INVENTION

Problems to be Solved by Invention

Problems of the Prior Art

According to the techniques described in Patent Documents 1 to 4, basically, a template image of a site (tracking object site) including a tumor or a lesion of a patient who is a target object of treatment is preliminarily created, and when actually irradiating the site with radiation, the template image and the actually captured image are compared with each other to specify the tracking object site.

However, since the X-ray fluoroscopic image is an image obtained by projecting a three-dimensional structure in the body, the tracking object site may be hidden by the bone (a non-tracking object, obstacle). In particular, when many bones are photographed in the X-ray image, the tracking object may be easily hidden by the bones. In addition, when capturing the X-ray image, a non-tracking object (obstacle) such as a bed frame (couch frame) on which a patient is immobilized or a fixture may be photographed in the X-ray image. Further, in X-ray therapy, by imaging the transmitted therapeutic X-ray by means of an electronic portal imaging device (EPID), a therapeutic target object site may be tracked to verify a positional accuracy. In this case, if the positional deviation of the therapeutic target object site is large, the therapeutic target object site may be hidden by a collimator for limiting irradiation to a normal tissue. As such, when creating a template image or capturing an X-ray fluoroscopic image, it may be difficult to see the therapeutic target object site due to the obstacle (such as a bone, couch frame or collimator, etc.). Therefore, tracking may be difficult in a tracking algorithm such as a conventional matching method. In addition, as a moving body tracking irradiation method, it is possible to enhance an accuracy of template matching by embedding the metal marker in the body for ensuring tracking, but it may be an invasive method and may place a burden on the patient.

A method of processing for subtracting information on a bone (a bone suppression method) by specifying a non-tracking object (obstacle) portion corresponding to the bone or the couch frame has also been reported.

However, in this processing method, a processing speed may be slow because there is a specific image processing on the bone and processing for subtracting bone image information, and it is difficult to track the X-ray irradiation position in which real-time properties are required. In addition, when subtracting information on the obstacle such as a bone, information up to the tracking object site including a part of the image information in the obstacle image due to being hidden by the obstacle, etc. is subtracted, such that an outer shape of the tracking object site on the image may be deviated from the outer shape of the actual tracking object site.

In addition, it is known that the shape of the tracking object to be captured changes with the breathing of the patient, but in the prior arts, when creating a template image, it may be difficult to specify the shape of a portion hidden by the obstacle such as a bone.

Further, the image of the X-ray to be captured may also have a difference between a bright portion and a dark portion, when capturing the template image and when irradiating radiation, that is, a difference in a so-called contrast. Thereby, even when comparing the template image and the X-ray fluoroscopic image at the time of radiation irradiation, the position of the tracking object may be unclear.

In addition, due to an unexpected motion such as coughing or sneezing of the patient, the tracking object may make a large movement (unexpected motion) beyond a range of the template image. However, in the techniques such as Patent Documents 3 and 4, when creating a template image, it may only cope with a periodic change such as breathing.

It is a technical object of the present invention to make it easy to specify a tracking object site without being affected by an obstacle, as compared to an image tracking method by template matching of the prior art.

Means for Solving Problems

In order to solve the above technical object, according to a first aspect of the present invention, there is provided an object tracking device an object tracking device including: a superimposed image creation unit configured to create a plurality of superimposed images in which each of a plurality of non-tracking object images which do not include an image feature of a tracking object is superimposed on a tracking object section image which includes the image feature of the tracking object; a discriminator creation unit configured to learn at least one of an image feature and position information of the tracking object, based on the plurality of superimposed images to create a discriminator; and a tracking object specifying unit configured to specify at least one of the image feature and the position information of the tracking object in a tracked image including the image feature of the tracking object, based on the discriminator and the tracked image.

An invention of a second aspect of the present invention is the object tracking device according to the first aspect of the present invention, including: an input unit configured to previously input a teacher image which specifies the image feature of the tracking object; and the discriminator creation unit configured to learn at least one of the image feature and the position information of the tracking object, based on the plurality of superimposed images and the teacher image to create a discriminator An invention of a third aspect of the present invention is the object tracking device according to the first or second aspect of the present invention, including a non-tracking object image edition unit configured to derive the number of non-tracking object images, based on a size of the image feature of the tracking object, a resolution of the image, and a preset tracking accuracy, so as to create the non-tracking object image according to the derived number.

An invention of a fourth aspect of the present invention is the object tracking device according to any one of the first to third aspects of the present invention, including: an image separation unit configured to separate and extract the tracking object section image which includes the image feature of the tracking object and the separation non-tracking object image which does not include the image feature of the tracking object, from a learning original image including the image feature of the tracking object; a non-tracking object image edition unit configured to edit the separation non-tracking object image to create the plurality of edited non-tracking object images; and the superimposed image creation unit configured to create the superimposed image based on the tracking object section image and the non-tracking object image.

An invention of a fifth aspect of the present invention is the object tracking device according to any one of the first to third aspects of the present invention, including: an image separation unit configured to separate and extract the tracking object section image which includes the image feature of the tracking object and the separation non-tracking object image which does not include the image feature of the tracking object, from an original image including the image feature of the tracking object; an obstacle image acquisition unit configured to acquire an image of an obstacle which is not included in the original image and is included in the tracked image; a non-tracking object image edition unit configured to edit at least one of the separation non-tracking object image and the image of the obstacle to create a plurality of edited non-tracking object images; and the superimposed image creation unit configured to create the superimposed image based on the tracking object section image and the non-tracking object image.

An invention of a sixth aspect of the present invention is the object tracking device according to the fourth or fifth aspect of the present invention, including the image separation unit configured to separate and extract the tracking object section image and the separation non-tracking object image, from the learning original image including the image feature of the tracking object, based on contrast information of the image feature of the tracking object.

An invention of a seventh aspect of the present invention is the object tracking device according to any one of the first to sixth aspects of the present invention, including a tracking accuracy evaluation unit configured to evaluate a tracking accuracy of the tracking object, based on an image for evaluation in which at least one of the image feature and the position information of the tracking object is preset, and the discriminator.

An invention of an eight aspect of the present invention is the object tracking device according to seventh aspect of the present invention, including the discriminator creation unit configured to increase the number of non-tracking object images to recreate the discriminator, when the tracking accuracy by the tracking accuracy evaluation unit does not reach a preset accuracy.

Advantageous Effects

According to the invention of the first aspect of the present invention, at least one of the region and the position of the tracking object site of the treatment may be easily specified compared to the image tracking method by template matching of the prior art.

According to the invention of the second aspect of the present invention, the processing may be speeded up compared to a case in which the teacher image is not used. According to the invention of the second aspect of the present invention, when there is the teacher image, the position and the shape of the image feature region of the tracking object in the teacher image have a correlation with the position and the shape of the image feature region of the tracking object included in the plurality of superimposed images, but there is no correlation with the position and the shape of the image feature of the obstacle other than the tracking object. The presence or absence of this correlation produces an effect of learning by distinguishing whether it is information required for tracking.

According to the invention of the third aspect of the present invention, the required and sufficient number of non-tracking object images may be created according to a size or resolution of the image and a tracking system.

According to the invention of the fourth aspect of the present invention, each subject such as a patient may learn depending on a difference in different backgrounds or obstacles, as compared to the case in which the separated non-tracking object image including a background object and the obstacle such as a bone to be an obstacle for tracking, is not used. That is, in the prior art, only discriminators created based on a large number of subjects may be realized, but tracking suitable for each of subjects may be performed in the present invention as compared to the prior arts.

According to the invention of the fifth aspect of the present invention, by adding the image of the obstacle not included in the original image, even when the obstacle not included in the original image is mixed into the tracked image during tracking the object, the accuracy of object tracking may also be improved. That is, conventionally, when an obstacle not included in the original image of such learning is mixed into the tracked image during tracking the object, the accuracy of object tracking is significantly reduced, but it is possible to perform tracking suitable for the individual tracked image in the present invention as compared to the prior arts.

According to the invention of the sixth aspect of the present invention, it is possible to automatically separate the tracking object and the non-tracking object based on the contrast information, and facilitate processing of separation, as compared to the case in which the tracking object is manually specified.

According to the invention of the seventh aspect of the present invention, the discriminator may be evaluated before an actual treatment.

According to the invention of the eighth aspect of the present invention, when the accuracy of the discriminator is insufficient, the discriminator may be recreated using the superimposed image in which the number of images is increased, and the accuracy of the discriminator may be improved.

BRIEF DESCRIPTION OF DRAWINGS

FIGS. 4A and 4B are views describing an example of learning a position of a tracking object, wherein FIG. 4A is a view describing an example of a plurality of superimposed images, and FIG. 4B is a view describing a case in which the superimposed images are superimposed.

FIG. 8 is a view describing experimental results of Example 1.

FIGS. 9A and 9B are views describing a range in which a tracking object moves with the lapse of time, wherein FIG. 9A is a view describing a conventional template method, and FIG. 9B is a view describing a learning method of Example 1.

FIGS. 10A and 10B are views describing when tracking a tumor which is a target object of treatment using an image captured by an EPID, wherein FIG. 10A is a view describing a state in which the tracking object is not hidden by a collimator, and FIG. 10B is a view describing a state in which the tracking object is partially hidden by the collimator.

MODE FOR CARRYING OUT INVENTION

Hereinafter, examples that are specific examples of the embodiment of the present invention will be described with reference to the drawings, but the present invention is not limited to the following examples.

In the following description using the drawings, members other than members necessary for the description will not be appropriately illustrated to facilitate the understanding.

EXAMPLE 1

Figure 1:
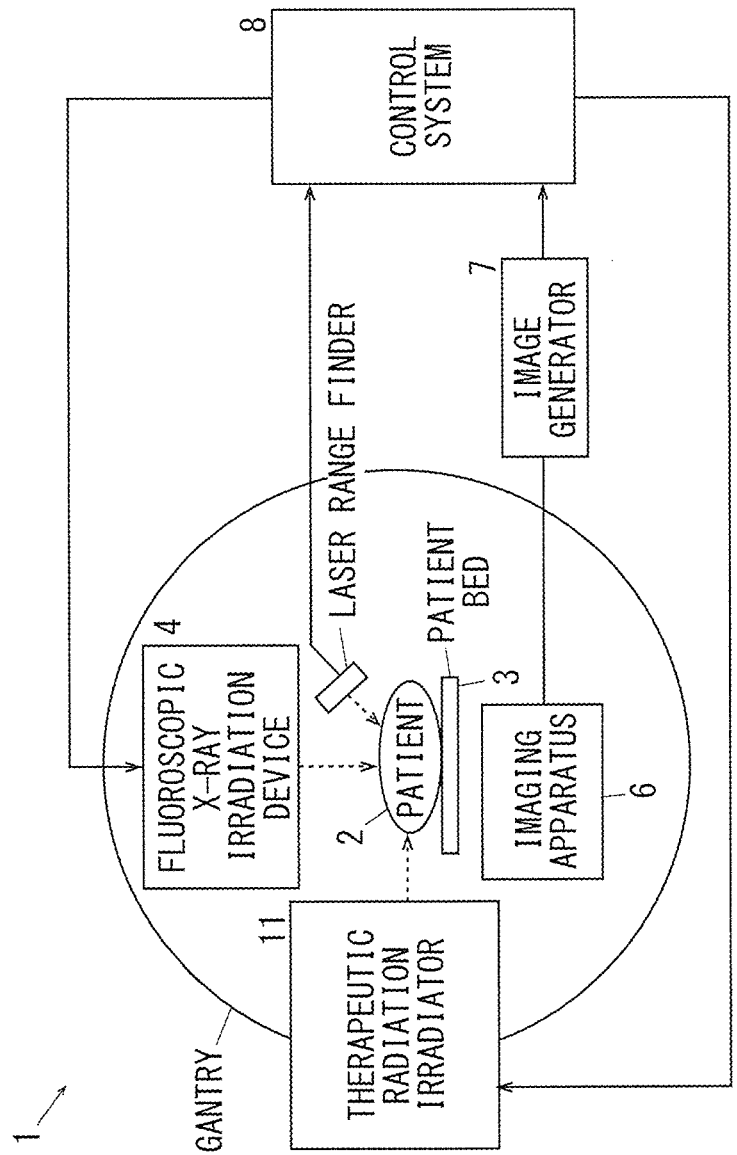
FIG. 1 is a view describing a radiation therapy machine to which an object tracking device of Example 1 of the present invention is applied.

FIG. 1 is a view describing a radiation therapy machine to which an object tracking device of Example 1 of the present invention is applied.

In FIG. 1, a radiation therapy machine 1 to which the object tracking device of Example 1 of the present invention is applied has a bed 3 on which a patient 2 who is a subject of treatment sleeps. A fluoroscopic X-ray irradiation device 4 is disposed above the bed 3. The fluoroscopic X-ray irradiation device 4 is configured to irradiate a patient with X-rays to capture an X-ray fluoroscopic image (a CT image). An imaging device 6 is disposed on a side opposite to the fluoroscopic X-ray irradiation device 4 with the patient 2 interposed therebetween. The imaging device 6 receives an X-ray transmitted through the patient and captures an X-ray fluoroscopic image. An image captured by the imaging device 6 is converted into an electrical signal by an image generator 7, and is input to a control system 8. In addition, the fluoroscopic X-ray irradiation device 4, the imaging apparatus 6, and the image generator 7 may employ any structure known in the art, for example, and it is preferable to employ a configuration that can create a three-dimensional CT image as described in Patent Documents 2 to 4, etc.

Further, a therapeutic radiation irradiator (therapeutic device) 11 is disposed on a side of the bed 3. The therapeutic radiation irradiator 11 is configured to receive a control signal from the control system 8. The therapeutic radiation irradiator 11 is configured to irradiate a preset position (an affected portion of the patient 2) with therapeutic radiation based on the input of the control signal.

(Description of Control System (Control Unit) of Example 1)

Figure 2:
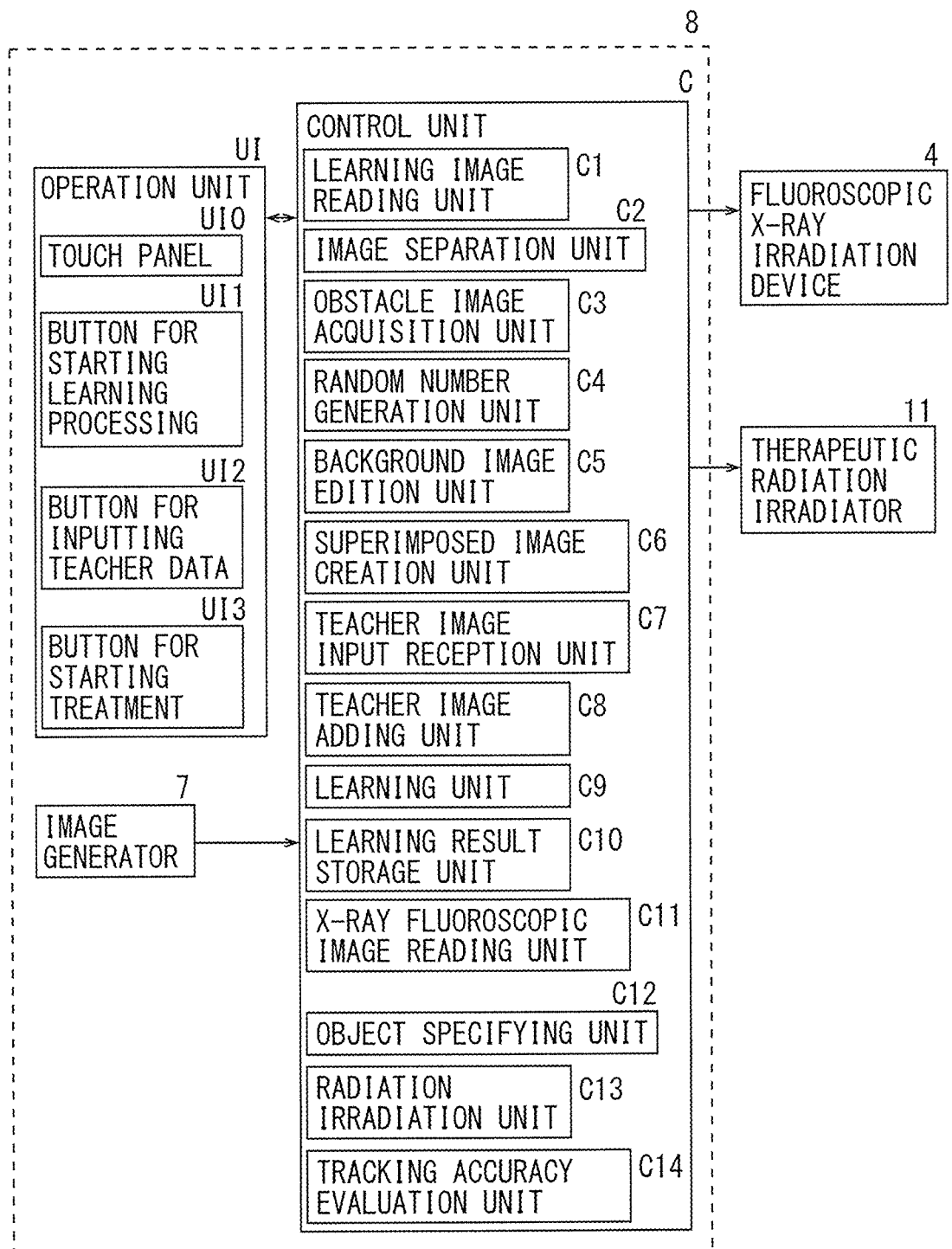
FIG. 2 is a block diagram illustrating each function of a control unit in the radiation therapy machine of Example 1.

FIG. 2 is a block diagram illustrating each function provided in the control unit of the radiation therapy machine of Example 1.

In FIG. 2, a control unit C of the control system 8 has an input/output interface I/O which performs input/output of signals with an outside. In addition, the control unit C has a read only memory (ROM) in which a program for performing required processing, information, and the like are stored. Further, the control unit C has a random access memory (RAM) for temporarily storing required data. Further, the control unit C includes a central processing unit (CPU) which performs processing according to a program stored in the ROM or the like. Therefore, the control unit C of Example 1 is configured by a small information processing apparatus, a so-called microcomputer. Thereby, the control unit C may realize various functions by executing the program stored in the ROM or the like.

(Signal Output Elements Connected to the Control Unit C)

The control unit C receives output signals from an operation unit UI, the image generator 7, and signal output elements such as a sensor (not illustrated).

The operation unit (a user interface) UI is an example of a display unit and includes a touch panel UI0 as an example of an input unit. In addition, the operation unit UI includes various input members such as a button UI1 for starting learning processing, a button UI2 for inputting teacher data, and a button UI3 for starting a treatment.

The image generator 7 inputs the CT image captured by the imaging device 6 to the control unit C. Further, the image generator 7 inputs, for example, 15 images (15 frames: 66 [ms/f]) per second.

(Controlled Elements Connected to the Control Unit C)

The control unit C is connected to the fluoroscopic X-ray irradiation device 4, the therapeutic radiation irradiator 11, and other control elements (not illustrated). The control unit C outputs control signals to the fluoroscopic X-ray irradiation device 4, the therapeutic radiation irradiator 11 and the like.

The fluoroscopic X-ray irradiation device 4 irradiates the patient 2 with X-rays for capturing an X-ray fluoroscopic image during learning or treatment.

The therapeutic radiation irradiator 11 irradiates the patient 2 with therapeutic radiation (X-ray) at the time of treatment.

(Functions of Control Unit C)

The control unit C has functions of executing the processing based on input signals from the signal output elements, and outputting the control signals to each control element. That is, the control unit C has the following functions.

Figure 3:
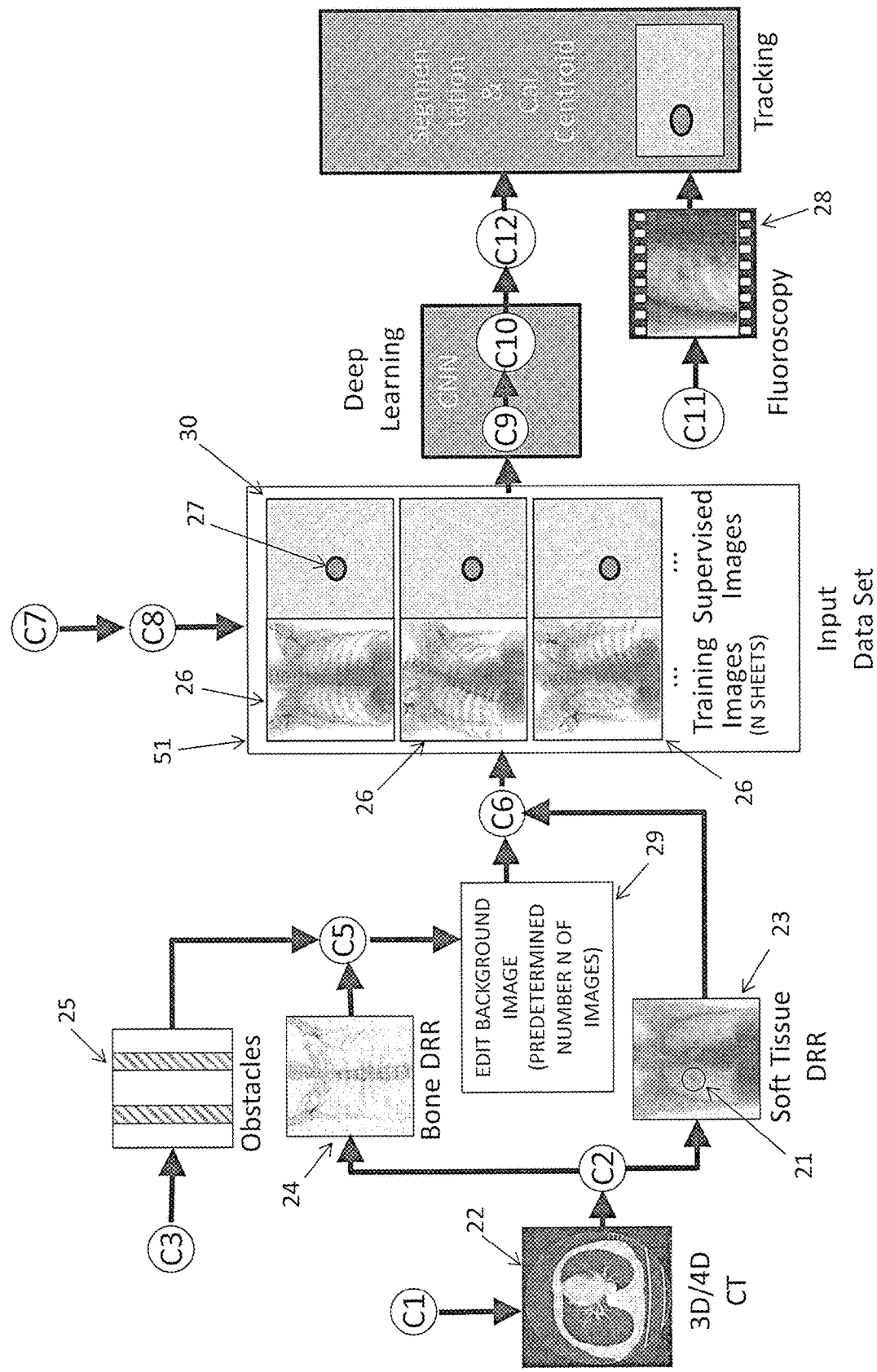
FIG. 3 is a view describing an example of processing in the control unit of Example 1.

FIG. 3 is a view describing an example of processing in the control unit of Example 1.

C1: Learning Image Reading Unit

The learning image reading unit C1 reads (reads-in) the CT image input from the image generator 7. The learning image reading unit C1 of Example 1 reads an image input from the image generator 7 when the button UI1 for starting learning processing is input. Further, in Example 1, reading of the CT image is performed during a preset learning period after the input of the button UI1 for starting learning processing is started. Furthermore, the learning image reading unit C1 of Example 1 forms a longitudinal-sectional image (not illustrated) from a learning original image (a plurality of cross-sectional images) including a tracking object image feature 21 (an arrangement pattern and an image region of pixel values representing a feature of a tumor which is the tracking object) illustrated in FIG. 3, then performs the following operations. Thereby, in Example 1, each of the units C2 to C10 related to learning executes image separation, editing, superposition, etc. based on each of images respectively read and stored in time sequence by the learning image reading unit C1. That is, in Example 1, learning processing is not performed in real time for capturing the CT image, but a processing speed may be improved by speeding up of the CPU, or the like, and if processing is possible even in real time, the processing may also be performed in real time.

C2: Image Separation Unit

The image separation unit C2 separates and extracts a soft tissue digitally reconstructed radiograph (DRR) image as an example of the tracking object section image 23 including the tracking object image feature 21, and a bone structure DRR image including an image feature of a bone structure as an example of a separation background image (non-tracking object image, separation non-tracking object image) 24 which does not include a region representing the feature of tracking object, such as the tracking object image feature 21, based on a learning original image 22 including the tracking object image feature 21. The image separation unit C2 of Example 1 separates the learning original image into the tracking object section image 23 (a first image, soft tissue DRR image) and the separation background image 24 (bone structure DRR image) based on the CT value which is contrast information of the CT image. In Example 1, as an example, the separation background image 24 is formed by a region having a CT value of 200 or more as the bone structure DRR image, and the tracking object section image 23 is formed by a region having a CT value of less than 200 as the soft tissue DRR image.

Further, as an example, Example 1 embodies a case, in which a tumor (tracking object) generated in a lung, that is, the target object of treatment is photographed in the tracking object section image 23 as the soft tissue DRR image, but for example, when the tracking object is an abnormal portion of a bone, etc., the bone structure DRR image is selected as the tracking object section image 23, and the soft tissue DRR image is selected as the separation background image 24. As such, for selection, the tracking object section image and the background image (non-tracking object image) is appropriately selected according to the background image including the tracking object and the obstacle.

For designation, the tumor (tracking object) may also be manually designated in such a way as to manually designate a region of the tumor on a screen. In addition, a configuration, in which the tumor is automatically discriminated in such a way as to automatically extract an object commonly photographed in a plurality of original images 22, may also be possible.

C3: Obstacle Image Acquisition Unit

The obstacle image acquisition unit C3 acquires an image 25 of an obstacle which is included when acquiring a tracked image 28 in the therapeutic radiation irradiator 11 and is different from the separation background image 24. In Example 1, as an obstacle image 25, X-ray images of the frame (couch frame) of the bed 3 and the fixture for fixing the patient to the bed 3 are previously stored in the storage medium, and the obstacle image acquisition unit C3 reads and acquires the image (obstacle image 25) of the couch frame or the fixture stored in the storage medium.

C4: Random Number Generation Unit

The random number generation unit C4 generates random numbers.

C5: Background Image Edition Unit (Non-Tracking Object Image Edition Unit, non-tracking object image creation unit)

The background image edition unit C5 is one example which edits at least one of position, enlargement/reduction, rotation, and light and darkness of the separation background image 24 or the obstacle image 25 with respect to the tracking object section image 23, thereby creating a background image (non-tracking object image) 29. The background image edition unit C5 of Example 1 edits at least one of the position, enlargement/reduction, rotation, and light and darkness based on the random numbers. In Example 1, specifically, by performing affine transformation, the separation background image 24 or the obstacle image 25 is moved in parallel, or by performing linear transformation (rotation, shearing, enlargement, reduction), and by changing each value of the affine transformation matrix based on the random numbers, the separation background image 24, or the like is edited to create the background image 29.

Further, for the light and darkness (contrast), an amount of light and darkness of the separation background image 24, or the like is changed in a light or darkness direction according to the random numbers. In Example 1, the background image edition unit C5 creates 100 edited background images as an example of a preset number, with respect to one separation background image 24 or the like. That is, 100 background images 29, in which the position, etc., of the separation background image 24, or the like is randomly edited by the random numbers, are created.

Furthermore, it is preferable that the number N of background images 29 to be created is set based on a size of the region of the image of the tracking object section image 23, the resolution of the image, and the preset tracking accuracy. As an example, when the image of the tracking object section image 23 has a size of 10 cm×10 cm, the resolution is 1 mm, and the required tracking accuracy is 10 times the resolution, it is possible to create 1000 background images 29, which are obtained by {10 (cm)/1 (mm)}×10 (times) =1000 (sheets).

C6: Superimposed Image Creation Unit

The superimposed image creation unit C6 creates a superimposed image 26 in which each of the background images 29 (an image obtained by performing edition such as rotation on the separation background image 24 or the obstacle image 25) is respectively superimposed on the tracking object section image 23.

C7: Teacher Image Input Reception Unit

The teacher image input reception unit C7 receives an input of a teacher image 30 including a teacher image feature 27 as an example of an image for teaching an object to be tracked, according to an input on the touch panel UI0 or an input on the teacher data input button UI2. Further, in Example 1, it is configured that, by displaying the learning original image (CT image) 22 on the touch panel UI0, and inputting by the teacher on the screen so as to surround the image feature of the tracking object which is the target object of treatment, the teacher image feature 27 can be determined.

C8: Teacher Image Adding Unit

The teacher image adding unit C8 adds (further superimposes) the teacher image 30 including the input teacher image feature 27 to the superimposed image 26.

Figure 4B:
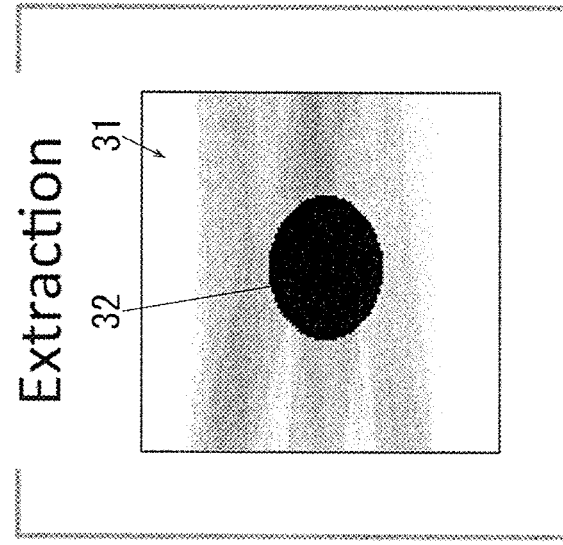
Figure 4A:
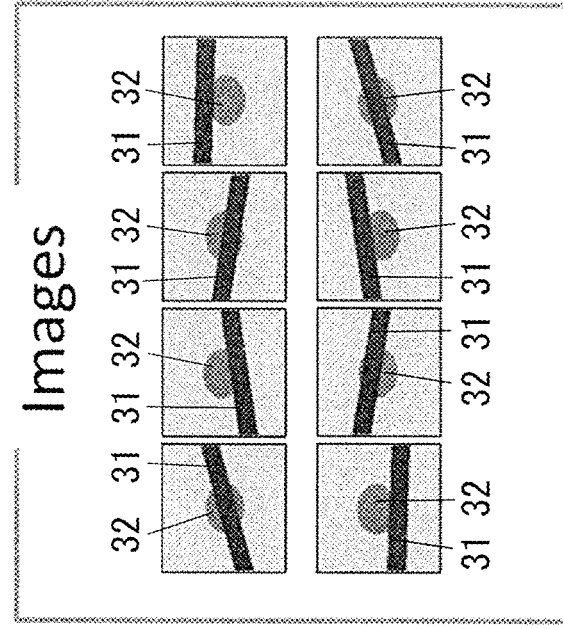

FIGS. 4A and 4B are views describing an example of learning a position of the tracking object, wherein FIG. 4A is a view describing an example of a plurality of superimposed images, and FIG. 4B is a view describing a case in which the superimposed images are superimposed.

C9: Learning Unit (Discriminator Creation Unit)

The learning unit C9 learns at least one of region information and position information of the tracking object image feature 21 in the image and creates a discriminator, based on a plurality of learning images 51 in which the teacher image 30 is added to the plurality of superimposed images 26. In addition, in Example 1, both the region and the position of the tracking object image feature 21 are learned. Further, in Example 1, a position of a center in the region of the tracking object image feature 21 is exemplified as the position of the tracking object image feature 21, but it may be changed to any position such as an upper end, lower end, right end, or left end of the region according to a design or specification.

In FIGS. 4A and 4B, in the learning unit C9 of Example 1, if each image is further superimposed on a plurality of superimposed images (see FIG. 4A), in which the image of the obstacle image feature 31 whose position, etc. is randomly edited are superimposed on the tracking object image feature 32, as illustrated in FIG. 4B, the tracking object image feature 32 whose position is not edited may be relatively emphasized (amplified), and the obstacle image feature 31 whose position etc. is random may be relatively suppressed (attenuated). Therefore, it is possible to learn the position and the outer shape of the tracking object image feature 32 in the CT image. In addition, although any conventionally known configuration may be employed as the learning unit C9, it is preferable to use so-called deep learning (neural network having a multilayer structure), and in particular, it is preferable to use a convolutional neural network (CNN). Caffe is used in Example 1 as an example of deep learning, but it is not limited thereto, and any learning unit (framework, algorithm, software) may be employed.

C10: Learning Result Storage Unit

The learning result storage unit C10 stores learning results of the learning unit C9. That is, the CNN optimized by learning is stored as a discriminator.

C11: X-Ray Fluoroscopic Image Reading Unit

The X-ray fluoroscopic image reading unit C11 reads the CT image (a third image) input from the image generator 7. The X-ray fluoroscopic image reading unit C11 of Example 1 reads the tracked image 28 input from the image generator 7 when the button UI3 for starting treatment is input.

C12: Object Specifying Unit

The object specifying unit C12 specifies the position of the tracking object in the tracked image 28, based on the learning results of the learning unit C9 and the tracked image 28 including the target object which is the tracking object. The object specifying unit C12 of Example 1 specifies the region information and the position information of the tracking object image feature 21 in the tracked image 28 (in this case, the X-ray fluoroscopic image) using the discriminator (CNN) optimized by learning, and outputs the specified region information and position information.

C13: Radiation Irradiation Unit

The radiation irradiation unit C13 controls the therapeutic radiation irradiator 11, such that, when the region and position of the tracking object image feature 21 specified by the object specifying unit C12 are included in a radiation range of therapeutic X-rays, it is irradiated with the therapeutic X-rays.

C14: Tracking Accuracy Evaluation Unit

The tracking accuracy evaluation unit C14 evaluates the tracking accuracy of tracking object, based on an image for evaluation (test image) in which at least one of the region and the position of the tracking object is preset, and the discriminator. In Example 1, tracking of the tracking object is performed by the discriminator using an image whose region and position of the tracking object are already known as the test image, and a deviation between the region and the position of the tracking object specified by the discriminator and the already known region and the position is evaluated. In a case of evaluation for the region, for example, a calculation of (the number of pixels whose positions coincide with each other)/(the total number of pixels of outer edge) is performed on each pixel of an outer edge of the region specified by the discriminator and a pixel of an outer edge of the tracking object in the test image, and if the calculated value exceeds a threshold (e.g., 90%), it is possible to evaluate that the accuracy of the discriminator is sufficient for the specification of the region. Similarly, in a case of evaluation for the position, if a deviation of the position of the tracking object (a center of gravity position) specified by the discriminator with respect to the position of the tracking object in the test image is within a threshold (e.g., 5 pixels), it is possible to evaluate that the accuracy of the discriminator is sufficient for the specification of the position. In addition, the evaluation method is not limited to the above description, and for example, any evaluation method such as a method, in which the region is calculated by deriving a correlation coefficient of the shapes of the outer shape, may be employed.

Further, in Example 1, if it is evaluated that the accuracy is insufficient by the tracking accuracy evaluation unit C14, the background image edition unit C5 creates the number (2N) of images twice the number N of images up to that time, and additionally creates the superimposed image using the added edited image, then the learning unit C9 recreates the discriminator using the increased superimposed image. Therefore, the accuracy of the recreated discriminator is improved. In addition, it is also possible to configure so as to automatically increase the edited image to continuously recreate the discriminator until the accuracy of the discriminator reaches the preset threshold, and it is also possible to manually increase the number of edited images and recreate the discriminator.

Further, the object tracking device of Example 1 includes the fluoroscopic X-ray irradiation device 4, the imaging apparatus 6, the image generator 7, the control system 8, and the units C1 to C14.

(Description of Flowchart of Example 1)

Next, a flow of control in the radiation therapy machine 1 of Example 1 will be described using a flow diagram, a so-called flowchart.

(Description of Flowchart of Learning Processing)

Figure 5:
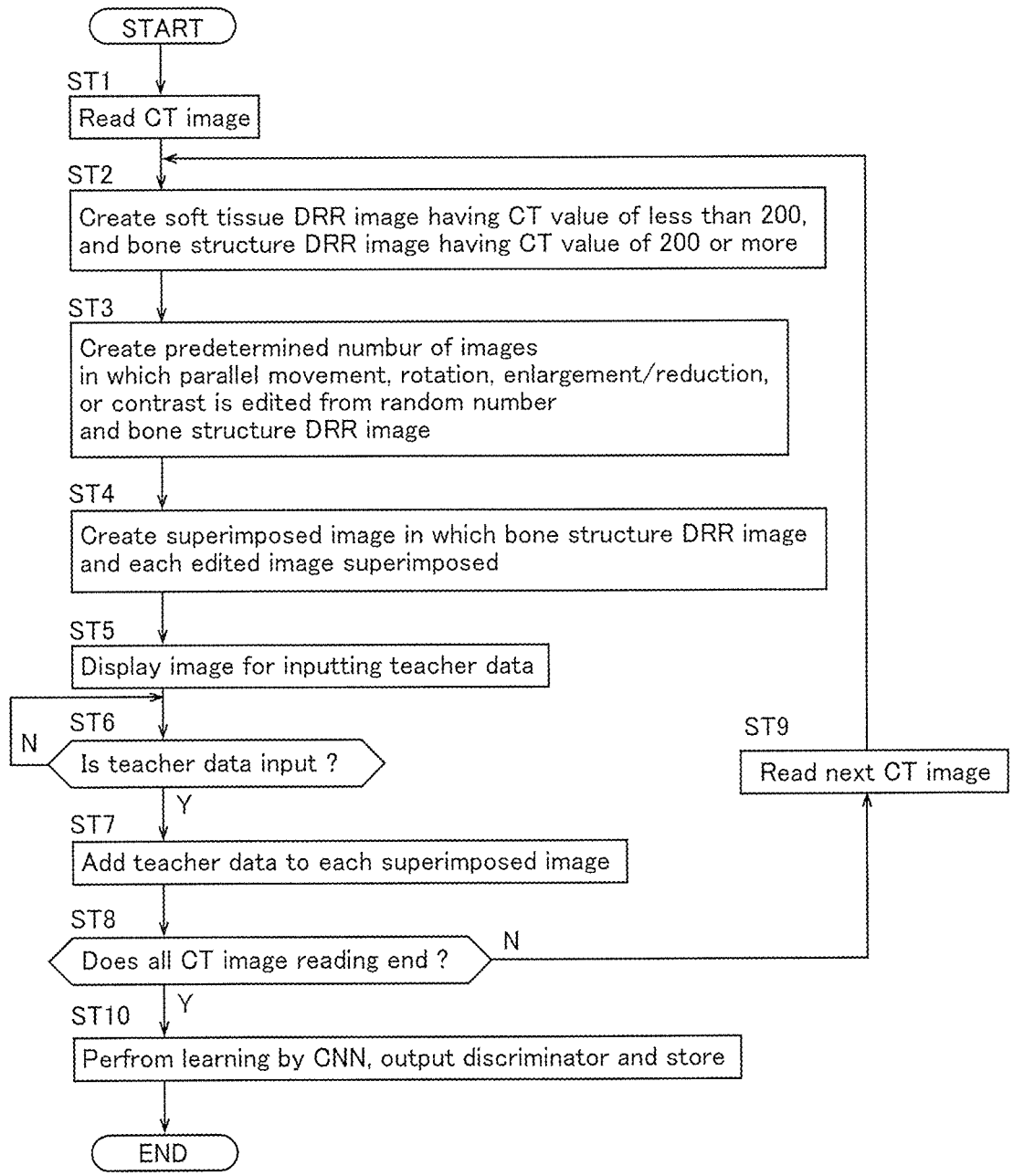
FIG. 5 is a view describing a flowchart of learning processing of Example 1.

FIG. 5 is a view describing a flowchart of learning processing of Example 1.

Processing of each step ST of the flowchart in FIG. 5 is performed according to the program stored in the control unit C of the radiation therapy machine 1. In addition, this processing is performed in parallel with other various processings of the radiation therapy machine 1. Further, processing of evaluating the tracking accuracy of the created discriminator according to an input of a user has a simple flowchart, and therefore will not be illustrated and described in detail.

The flowchart illustrated in FIG. 5 is started by an input of the button UI1 for starting learning processing.

In ST1 of FIG. 5, the CT image (original image 22) is read.

Then, the processing proceeds to ST2.

In ST2, the tracking object section image 23 having a CT value of less than 200 and the separation background image 24 having a CT value of 200 or more are created from the original image 22. Then, the processing proceeds to ST3.

In ST3, a predetermined number N of edited images, in which parallel movement, etc. is edited, are created from the random numbers and the separation background image 24. Then, the processing proceeds to ST4.

In ST4, the superimposed image 26 in which the tracking object section image 23 and each edited image are superimposed is created. Then, the processing proceeds to ST5.

In ST5, an image for inputting the teacher data (teacher image feature 27) is displayed on the touch panel UI0. Then, the processing proceeds to ST6.

In ST6, it is determined whether the teacher data (teacher image feature 27) is input. When it results in yes (Y), the processing proceeds to ST7, and if it results in no (N), ST6 is repeated.

In ST7, the teacher data (teacher image feature 27) is added to each superimposed image 26. Then, the processing proceeds to ST8.

In ST8, it is determined whether the learning period ends. If it results in no (N), the processing proceeds to ST9, and when it results in yes (Y), the processing proceeds to ST10.

In ST9, the next CT image (original image 22) is read. Then, the processing returns to ST2.

In ST10, learning is performed by the CNN, and the discriminator (optimized CNN) is output and stored. Then, the learning processing ends.

(Description of Flowchart of Tracking Processing)

Figure 6:
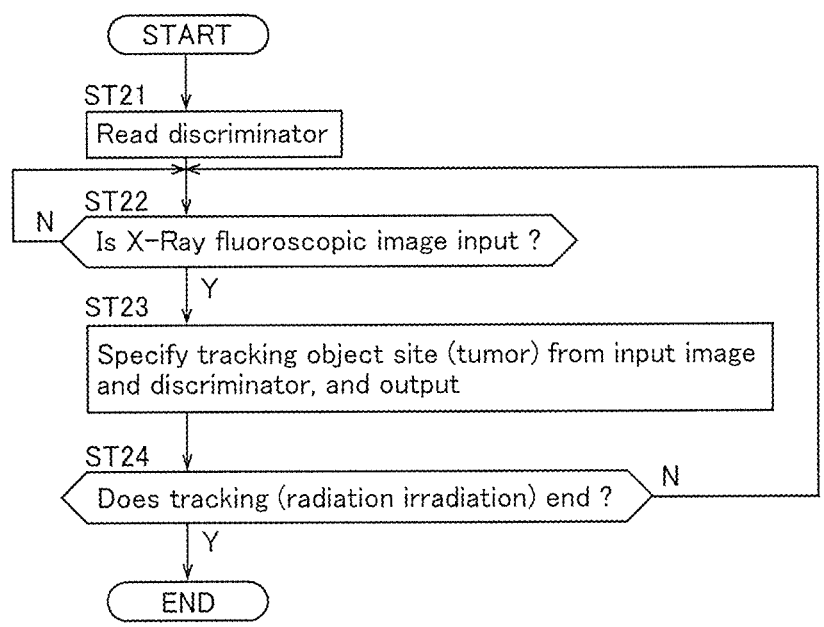
FIG. 6 is a view describing a flowchart of tracking processing of Example 1.

FIG. 6 is a view describing a flowchart of tracking processing of Example 1.

Processing of each step ST of the flowchart in FIG. 6 is performed according to the program stored in the control unit C of the radiation therapy machine 1. In addition, this processing is performed in parallel with other various processings of the radiation therapy machine 1. Further, the X-ray irradiation processing is processing that irradiates with X-rays when the position of the tracking object reaches a preset irradiation position, and does not irradiate in the other cases, and therefore will not be illustrated and described in detail. Furthermore, as the X-ray irradiation processing, it is also possible to employ the conventionally known techniques described in Patent Documents 1 to 4.

The flowchart illustrated in FIG. 6 is started by an input of the button UI3 for starting treatment.

In ST21 of FIG. 6, the discriminator (optimized CNN) is read. Then, the processing proceeds to ST22.

In ST22, it is determined whether the X-ray fluoroscopic image is input. When it results in yes (Y), the processing proceeds to ST23, and if it results in no (N), ST22 is repeated.

In ST23, the position of the tracking object (target object of treatment) is specified from the input image (X-ray fluoroscopic image) and the discriminator, and is output. Then, the processing proceeds to ST24.

In ST24, it is determined whether the tracking processing, that is, the irradiation processing of the therapeutic X-ray ends. If it results in no (N), the processing returns to ST22, and when it results in yes (Y), the tracking processing ends.

(Operation of Example 1)

Figure 7:
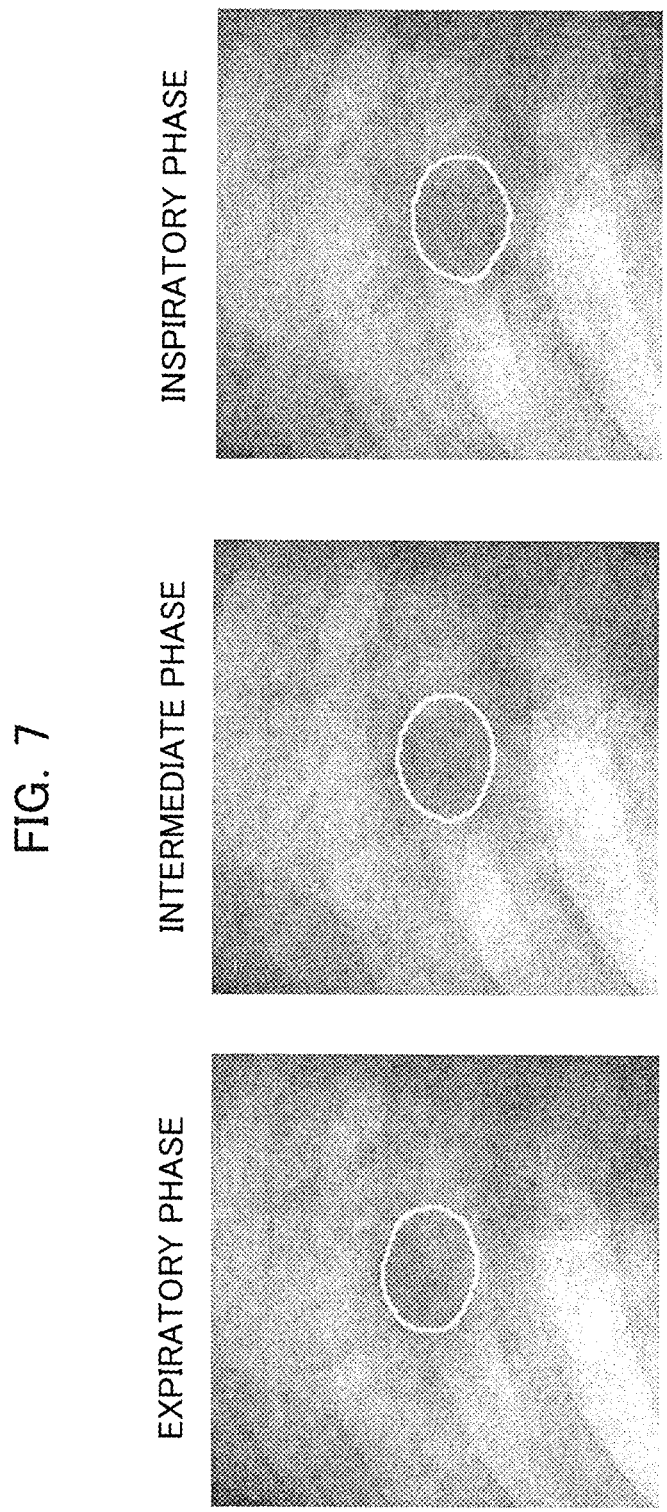
FIG. 7 is a view describing tracking results of a tumor in the radiation therapy machine of Example 1.

FIG. 7 is a view describing tracking results of a tumor in the radiation therapy machine of Example 1.

In the radiation therapy machine 1 of Example 1 having the above-described configuration, the soft tissue DRR image as the tracking object section image 23 including the tracking object image feature 21 and the bone structure DRR image as the separation background image 24 which does not include the tracking object are separated from the original image 22, and the separation background image 24 (bone structure DRR image) is randomly edited (processed), and then superimposed on the tracking object section image 23 (soft tissue DRR image). Therefore, it is easy to clearly recognize the position and the shape of the tracking object image feature 21 at the time of learning. When an obstacle such as a couch frame is photographed in the original image 22, the image feature is learned in a state of being separated from the original image 22 and included in the separation background image 24 (bone structure DRR image), such that the influence of the obstacle such as a couch frame is also suppressed at the time of learning. In addition, even when the obstacle to be learned is a surgical instrument, etc. that enters the body such as a catheter, the catheter, etc. that has entered the body and been photographed may be determined as the obstacle, and may be easily separated from the tracking object. Thereby, the influence of the obstacle in the body may also be suppressed when tracking the object in a situation in which the obstacle such as a catheter has entered the body.

Therefore, in the radiation therapy machine 1 of Example 1, compared to the method of creating a template image of the prior art, in which the outer shape may become unclear due to the influence of the bone, etc., the position and the outer shape (region) of the tracking object (target object of treatment) may be easily specified. Therefore, as illustrated in FIG. 7, even if the bones (non-tracking object, obstacle) are photographed in the fluoroscopic image, and even if the position or the outer shape of the tumor changes in an expiratory phase, an intermediate phase, or an inspiratory phase with the breathing of the patient, it is possible to accurately track the tumor. That is, not only the position of the tumor but also the shape of the tumor may be tracked in real time.

In addition, since a discriminator corresponding to a particular patient is created based on the original image 22, that is, the image of the patient, as compared to a case of using a versatile technique (template image) created based on data of many patients, it is possible to create a highly accurate discriminator according to the patient. Although individual differences in the shapes of bones are small, there are individual differences in the soft tissues (such as blood vessel travel or the shape of tumor), such that learning may not be effectively performed even when using images of other people. That is, when learning is performed using the images of many patients at random, the learning proceeds so that the features of each patient are ignored, and thus the accuracy is likely to be reduced. On the other hand, in Example 1, the discriminator is created for a particular patient, and the accuracy is improved.

FIG. 8 is a view describing experimental results of Example 1.

In FIG. 8, an experiment for tracking the tracked object was performed using test data. Experimental Example 1 adopts the configuration of Example 1. In Comparative Example 1, an experiment was performed using only the soft tissue DRR image by a conventional template method. In Comparative Example 2, an experiment was performed using a common DRR image (soft tissue DRR image+bone structure DRR image) by the conventional template method. The experimental results are illustrated in FIG. 8.

In FIG. 8, in Experimental Example 1, an average of pixels in error in tracking of the tracking object is 0.22 [pixel], a standard deviation is 1.7, a correlation coefficient is 0.997, and a Jaccard coefficient is an average of 0.918 (maximum 0.995, and minimum 0.764), and then the tracking accuracy of the tracking object was high, and good results were obtained. On the other hand, in Comparative Example 1, the average of the pixels in error was 4.4 [pixel], the standard deviation was 10, and the correlation coefficient was 0.113. In Comparative Example 2, the average of the pixels in error was 3.9 [pixel], the standard deviation was 9.1, and the correlation coefficient was 0.256. Therefore, in the configuration of Example 1 (Experimental Example 1), it is confirmed that the tracking accuracy is improved compared to the conventional cases (Comparative Examples 1 and 2). If one pixel is 1 mm, the average tracking error is 4 mm or more in the prior art because the average error is about 4 pixels, but in Example 1, the average tracking error is 0.22 pixels, which indicates an improvement to 0.22 mm or less.

Further, in Example 1, since the teacher data (teacher image feature 27) is used, it is possible to perform learning with sufficient accuracy in which the data of the superimposed image 26 required for learning is about 2000 sheets. In addition, although learning (deep learning) is possible without the teacher data, a large number of superimposed images 26 necessary to learn is required. Thereby, in the case of absence of the teacher data, the time for creating the superimposed image 26 and the time taken to learn are longer than the case of the presence of the teacher data, but in Example 1, since the teacher data (teacher image feature 27) is used, it is possible to perform the processing in a short time. Further, in Example 1, separation of the image, editing based on the random numbers, and creation of 2000 superimposed images may be performed in about one minute. In addition, deep learning could be processed in about 90 minutes. Further, in Example 1, processing for specifying (tracking) the position of the target object at the time of X-ray therapy was also possible in 25 ms per image. Furthermore, when the bone suppression method described in the background art of the present disclosure was performed by tracking processing, it took 15 seconds per image. Therefore, the processing speed during tracking has been increased by 600 times compared to the prior art.

Further, in Example 1, the tracking object section image 23 (soft tissue DRR image) and the separation background image 24 (bone structure DRR image) are separated from the original image 22 based on CT values, then edited and processed. Therefore, it is possible to learn according to the patients.

In addition, in Example 1, when editing the separation background image 24, the light and darkness (contrast) is also edited. Therefore, even if the contrasts are different between when the learning original image 22 is captured and when the X-ray fluoroscopic image for treatment is captured, learning is finished and it is easy to track even in a situation in which the contrasts are different. In addition, if learning is performed using an image in which not only the contrast of the separation background image 24 but also the entire contrast of the original image 22 are changed, the tracking accuracy may be further improved.

Further, in Example 1, the separation background image 24 or the obstacle image 25 is randomly edited. For accurate learning, it is sufficient when there are sufficient data uniformly distributed, but if preparing in advance without editing at random, it is troublesome and time-consuming. On the other hand, in Example 1, the separation background image 24 separated from the original image 22, or the obstacle image 25 added according to the therapeutic radiation irradiator 11 is randomly edited by random numbers, and it is possible to easily align the sufficient number of uniformly distributed data.

Generally, increasing the number of learning images by luminance conversion, geometric conversion, etc. of the original image is called "data expansion." The data expansion is used to prevent over-learning. This data expansion is used to prevent the generalization performance from deteriorating by learning too many detailed features due to overlearning. However, since these linear transformations can be restored to the original image by a simple transformation, an increase in images up to several tens of times is limited at best. That is, the effect of non-linear transformation is essential for data expansion of several hundred times or more. In Example 1, the superimposed images 26 are nonlinearly converted as a whole. Therefore, it is considered that there is no decrease in the generalization performance even with data expansion of several hundred times or more.

Further, in Example 1, when performing learning, learning is performed on the CT image of a predetermined learning period. That is, learning is performed on a so-called 4DCT, which is the CT image in which an element of time (a fourth dimension) is also added, in addition to an element of space (three dimensions).

Therefore, it is possible to accurately track the position and the outer shape of the tracking object which fluctuates in time due to breathing.

Figure 9A:
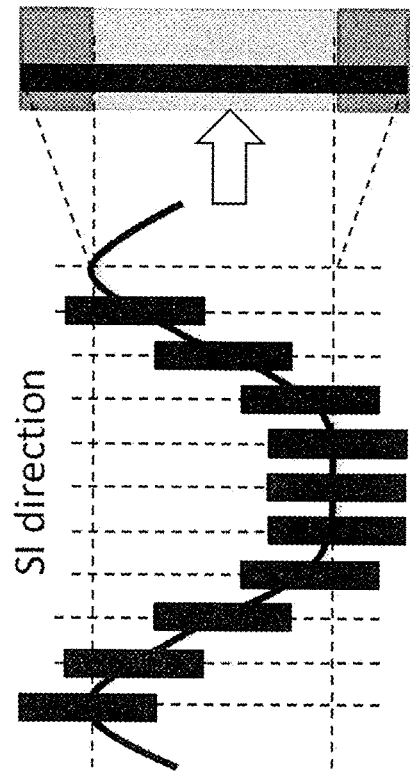
Figure 9B:
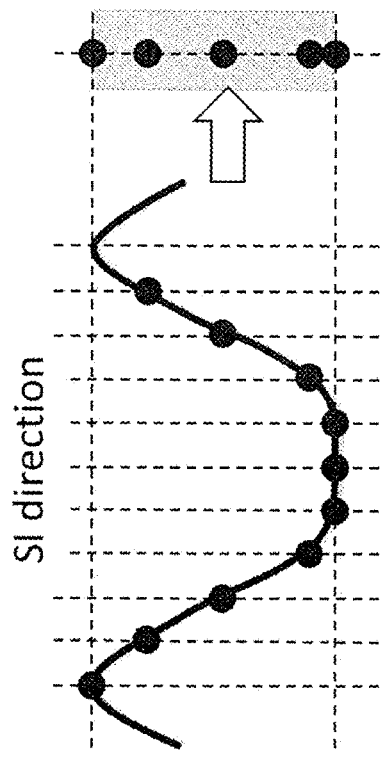

FIGS. 9A and 9B are views describing a range in which the tracking object moves with the lapse of time, wherein FIG. 9A is a view describing the conventional template method, and FIG. 9B is a view describing the learning method of Example 1.

In the conventional template method, as illustrated in FIG. 9A, since the positions of the obstacle (bone) and the tracking object in the CT image at each time are learned, the range in which the tracking object moves as a whole is the range photographed in the CT image, that is, learning is performed only in the range which fluctuates by breathing. On the other hand, in Example 1, in the CT image at each time, the separation background image 24 etc. is randomly edited, and a situation, in which the relative positions of the tracking object with respect to the non-tracking objects such as bones and couch frames etc., and the obstacles are variously different, is learned. That is, when viewing on the basis of the bone, etc., learning is performed on a situation in which the tracking object is at various positions (a situation having a positional width), and this learning is performed on each time. Therefore, as illustrated in FIG. 9B, for the range in which the tracking object moves as a whole, learning is performed also in a range exceeding the range photographed in the CT image, that is, a range exceeding the range moving by breathing. Therefore, in Example 1, when performing learning, a situation, in which the tracking object is relatively deviated with respect to the bone, etc., is learned, such that it is possible to cope with the situation of the unexpected motion beyond the range of movement due to breathing (coughing or sneezing) acquired by the 4DCT.

Furthermore, in Example 1, evaluation of the created discriminator is performed by the tracking accuracy evaluation unit C14. Therefore, before performing the treatment of actually irradiating with radiation, it is possible to evaluate the accuracy of the created discriminator, and it is possible to confirm in advance before the treatment whether the accuracy of the discriminator is sufficient. Then, if the accuracy is insufficient, it is possible to execute recreation of the discriminator. Therefore, the treatment may be performed using the discriminator having a sufficient accuracy, and the treatment accuracy may be improved, as well as exposing the patient to extra radiation may also be reduced as compared to the case of using an insufficient discriminator.

Figure 10A:
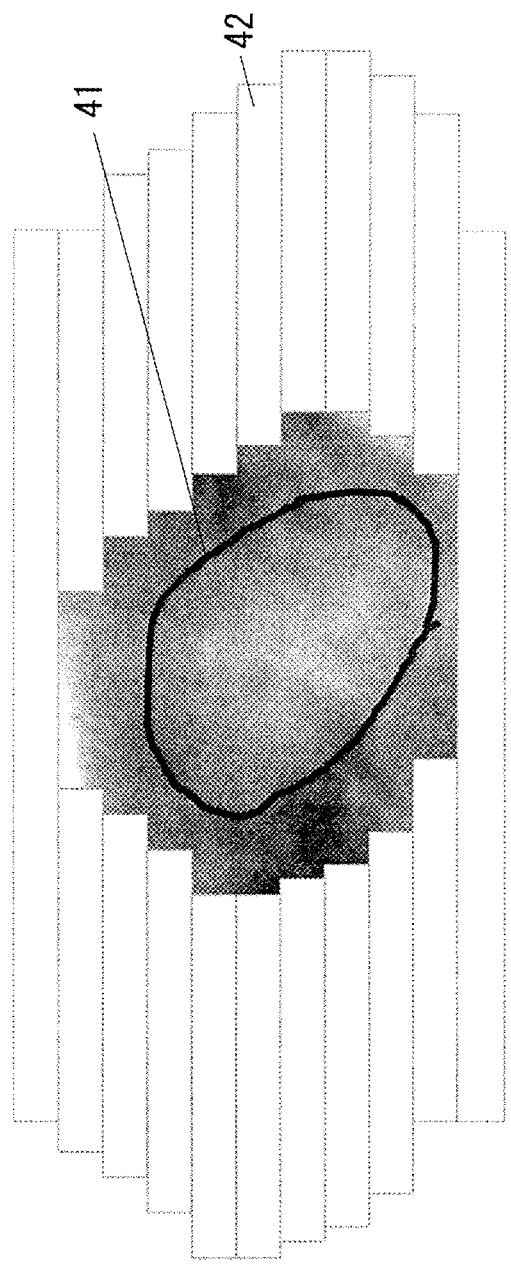
Figure 10B:
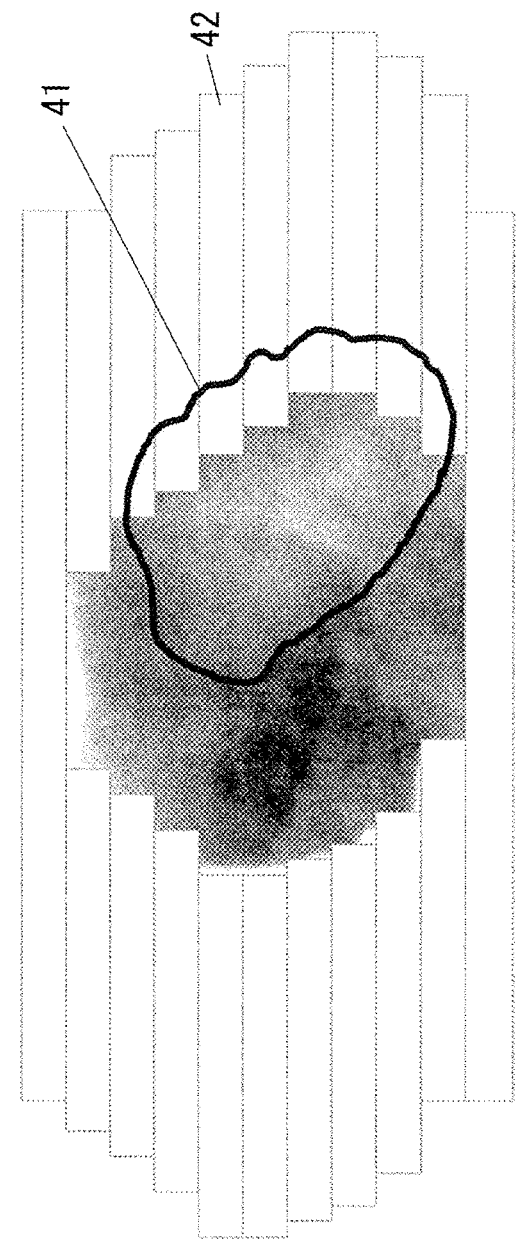

FIGS. 10A and 10B are views describing when tracking a tumor which is the target object of treatment using an image captured by an EPID, wherein FIG. 10A is a view describing a state in which the tracking object is not hidden by a collimator, and FIG. 10B is a view describing a state in which the tracking object is partially hidden by the collimator.

In FIGS. 10A and 10B, when applying to the EPID, a collimator 42 may be photographed as an obstacle with respect to the tracking object image feature 41. Then, depending on body movement such as breathing of the patient, there may be a case of changing between a state in which the tracking object image feature 41 is not hidden by the collimator 42 (FIG. 10A), and a state of being partially hidden (FIG. 10B). In such a case, when tracking is performed using the conventional template, the accuracy of estimating the outer shape of the tracking object image feature 41 in a hidden state is decreased. On the other hand, in Example 1, the obstacle image 25 such as a collimator is added and learned, and even if there is an obstacle such as the collimator 42, it is possible to accurately track the outer shape of the tracking object image feature 41.

Although the examples of the present invention have been described above in detail, the present invention is not limited to the above-described examples, and various modifications may be made within the scope of the present invention described in the claims. Modified examples (H01) to (H012) of the present invention will be described as an example below.

(H01) In the above examples, the configuration of using the CT image as the original image, the soft tissue DRR image, and the bone structure DRR image has been described as an example, but the present invention is not limited thereto. For example, an ultrasound image, MRI image, PET image, etc. may also be used.

That is, the present invention is not limited to the image captured by X-rays, and it is also possible to use an image captured by a magnetic resonance imaging (MRI) apparatus or an ultrasonic examination (echo).

In addition, the configuration, in which the separation of the soft tissue DRR image and the bone structure DRR image is performed according to the CT value, has been described as an example. However, when the CT image is not used, it is possible to set an appropriate threshold for a parameter that can separate an image in which the tracking object is photographed and an image in which the tracking object is not photographed in each image.

(H02) In the above examples, the tumor is exemplified as the tracking object (important site) using the image, and the bone, couch frame, and the like are exemplified as an unimportant site, but the present invention is not limited thereto. For example, in a plurality of images captured by a monitoring camera in the past, it may also be configured to track person by learning a person (important, tracking object) with respect to the background (non-important, non-tracking object).

(H03) In the above examples, it is preferable to use the teacher data (teacher image feature 27), but it may also be configured not to use such data. In this case, by increasing the number of superimposed images, it is possible to create the discriminator using an object appearing at almost the same position in the superimposed image as a tumor (important portion).

(H04) In the above examples, the configuration for performing parallel movement, enlargement/reduction, rotation, shearing, and editing of light and darkness has been described as an example, but it is not limited thereto. It is also possible to decrease or increase the content (parallel movement, enlargement/reduction, and the like) to be edited.

(H05) In the above examples, it is preferable to employ the configuration in which editing is performed based on the random numbers, but it may also be configured by preparing a previously superimposed image (corresponding to the bone structure DRR image).

(H06) In the above examples, the configuration for tracking both the region and the position of the tracking object (tumor) has been described as an example, but it is not limited thereto. For example, it may also be configured to track only the region or only the position. Further, it is also possible to perform learning so as to track elements other than the region and the position, such as brightness and color.

(H07) In the above examples, it is preferable to have the function of evaluating the tracking accuracy, but it may also be configured not to have such a function.

(H08) In the above examples, the tumor as the tracking object and the bone as the obstacle have been described as an example, but it is not limited thereto. For example, when confirming a posture of the patient at the time of treatment, it is also possible to use the bone as the tracking object and the soft tissue as the obstacle.

(H09) In the above examples, the DRR image is not limited to the projection angle exemplified in the examples, and it is possible to select projection in any angular direction.

(H010) In the above examples, the configuration in which tracking is performed without using a marker has been described as an example, but it is not limited thereto. The position of the marker may be learned using the X-ray image, etc. in which the marker is embedded, and even if the marker is hidden by the obstacle, the position and the outer shape thereof may be accurately discriminated and tracked.

(H011) In the above examples, the case in which there is one tumor, etc. which is the tracking object has been described as an example, but it may also be applied to a case in which there are a plurality of tracking objects. For example, when using an image having a gradation of 2 bits (22=4 gradations) or more as the teacher image, it is possible to cope with the case in which there are a plurality of tracking objects, by learning using one teacher image which is distinguished by changing the gradations in the first tracking object and the second tracking object. That is, generally, the teacher image is a labeled image representing region division, and the pixel value (gradation) is used as a label value. In the case of a simple binarized image, it may be expressed by one bit (0, 1), but in order to label and distinguish a plurality of regions, gradations of two or more bits are required. Further, for example, it is also possible to individually track by setting one of two tracking objects as a tracking object image feature without a marker and the other as the tracking object image feature in which the marker is embedded.

(H012) In the above examples, the configuration in which the tracking object device according to the present invention is applied to the radiation therapy machine 1 has been described as an example, but it is not limited thereto. For example, in the therapeutic device for crushing gallstones with ultrasonic waves, it is possible to apply to any device that requires precise tracking by using for tracking the position of gallstones, or using for tracking a photosensitive substance in photodynamic therapy (PDT), etc.

The invention claimed is:

1. An object tracking device comprising:
    a superimposed image creation unit configured to create a plurality of superimposed images in which each of a plurality of non-tracking object images which do not include an image feature of a tracking object is superimposed on a tracking object section image which includes the image feature of the tracking object;
    a discriminator creation unit configured to learn at least one of an image feature and position information of the tracking object, based on the plurality of superimposed images to create a discriminator; and
    a tracking object specifying unit configured to specify at least one of the image feature and the position information of the tracking object in a tracked image including the image feature of the tracking object, based on the discriminator and the tracked image.

2. The object tracking device according to claim 1, comprising:
    an input unit configured to previously input a teacher image which specifies the image feature of the tracking object; and
    the discriminator creation unit configured to learn at least one of the image feature and the position information of the tracking object, based on the plurality of superimposed images and the teacher image to create a discriminator.

3. The object tracking device according to claim 1, comprising a non-tracking object image edition unit configured to derive the number of non-tracking object images, based on a size of the image feature of the tracking object, a resolution of the image, and a preset tracking accuracy, so as to create the non-tracking object image according to the derived number.

4. The object tracking device according to claim 1, comprising:
    an image separation unit configured to separate and extract the tracking object section image which includes the image feature of the tracking object and the separation non-tracking object image which does not include the image feature of the tracking object, from a learning original image including the image feature of the tracking object;
    a non-tracking object image edition unit configured to edit the separation non-tracking object image to create the plurality of edited non-tracking object images; and the superimposed image creation unit configured to create the superimposed image based on the tracking object section image and the non-tracking object image.

5. The object tracking device according to claim 1, comprising:
an image separation unit configured to separate and extract the tracking object section image which includes the image feature of the tracking object and the separation non-tracking object image which does not include the image feature of the tracking object, from an original image including the image feature of the tracking object;
an obstacle image acquisition unit configured to acquire an image of an obstacle which is not included in the original image and is included in the tracked image;
a non-tracking object image edition unit configured to edit at least one of the separation non-tracking object image and the image of the obstacle to create a plurality of edited non-tracking object images; and
the superimposed image creation unit configured to create the superimposed image based on the tracking object section image and the non-tracking object image.

6. The object tracking device according to claim 4, comprising the image separation unit configured to separate and extract the tracking object section image and the separation non-tracking object image, from the learning original image including the image feature of the tracking object, based on contrast information of the image feature of the tracking object.

7. The object tracking device according to claim 1, comprising a tracking accuracy evaluation unit configured to evaluate a tracking accuracy of the tracking object, based on an image for evaluation in which at least one of the image feature and the position information of the tracking object is preset, and the discriminator.

8. The object tracking device according to claim 7, comprising the discriminator creation unit configured to increase the number of non-tracking object images to recreate the discriminator, when the tracking accuracy by the tracking accuracy evaluation unit does not reach a preset accuracy.

\* \* \* \* \*